United States Patent
Miyazawa et al.

(10) Patent No.: US 7,348,424 B2
(45) Date of Patent: Mar. 25, 2008

(54) POLYSACCHARIDE CONTAINING PHOSPHORYLCHOLINE GROUP AND PROCESS FOR PRODUCING THE SAME

(75) Inventors: Kazuyuki Miyazawa, Yokohama (JP); Toshio Yanaki, Yokohama (JP); Francoise M. Winnik, Westmount (CA)

(73) Assignee: Shiseido Company, Ltd., Tokyo (JP)

( * ) Notice: Subject to any disclaimer, the term of this patent is extended or adjusted under 35 U.S.C. 154(b) by 550 days.

(21) Appl. No.: 10/506,771

(22) PCT Filed: Apr. 8, 2003

(86) PCT No.: PCT/JP03/04430

§ 371 (c)(1),
(2), (4) Date: Sep. 7, 2004

(87) PCT Pub. No.: WO03/085001

PCT Pub. Date: Oct. 16, 2003

(65) Prior Publication Data

US 2005/0222405 A1    Oct. 6, 2005

(30) Foreign Application Priority Data

Apr. 9, 2002    (JP) .............................. 2002-106356

(51) Int. Cl.
*C07H 5/04*    (2006.01)
*C07H 5/06*    (2006.01)
*C08B 37/00*    (2006.01)

(52) U.S. Cl. ...................... 536/55.1; 536/53; 536/55.3

(58) Field of Classification Search .................... None
See application file for complete search history.

(56) References Cited

FOREIGN PATENT DOCUMENTS

EP    0 580 871 A1    12/1993
JP    10237102 A  *   9/1998

OTHER PUBLICATIONS

Ishihara K: "Novel Polymeric Materials For Obtaining Blood-compatible Surfaces", Trends In Polymer Science, Elsevier Science Publishers B. V. Amsterdam, NL, vol. 5, No. 12, Dec. 1997, pp. 401-407, XP004098788.

* cited by examiner

*Primary Examiner*—Shaojia Anna Jiang
*Assistant Examiner*—Layla Bland
(74) *Attorney, Agent, or Firm*—Townsend & Banta

(57) ABSTRACT

The present invention is a method for manufacturing a phosphorylcholine group-containing polysaccharide wherein the aldehyde derivative-containing compound obtained by the oxidative ring-opening reaction of glycerophosphorylcholine is added to a polysaccharide containing amino groups as well as a new polysaccharide having phosphorylcholine groups obtained from this manufacturing method.

The object of the present invention is to provide a phosphorylcholine group-containing polysaccharide that is superior in biocompatibility and moisture retention, and is useful as a polymer material for medical use, as well as a simple method of manufacturing it.

The polysaccharide of the present invention is utilized, for example, in artificial organs, biomembranes, coating agents for medical tools, drug delivery, and in cosmetics.

1 Claim, 16 Drawing Sheets

$R_2$=H, or $R_2$=H, or

R=H or CH$_2$-CONHCH$_2$CH$_2$NH$_2$

R=H or CH$_2$COOH

R=H or CH$_2$CONHCH$_2$CH$_2$NH$_2$

R = H, or

R = H, or $R_2$ = H, or or $CH_2CONHCH_2CH_2NHCO\text{-}C_{12}H_{25}$

R =H, or

—H$_2$C—C(=O)—NH—CH$_2$·CH$_2$ or CH$_2$CONHCH$_2$CH$_2$NHCO-C$_{18}$H$_{37}$

R=

$H_3C-N^+(CH_3)_2-CH_2-CH_2-O-P(=O)(O^-)-O-CH_2-CH_2-$ or

CF$_3$-CF$_2$-CF$_2$-CF$_2$-CF$_2$-CF$_2$-CF$_2$-CH$_2$-

R = H, or or

-CH₂CONHCH₂CH₂NHCO-C₁₂H₂₅

R=H or CH₂CH₂OH

R=H or CH$_2$CH$_2$OH

POLYSACCHARIDE CONTAINING PHOSPHORYLCHOLINE GROUP AND PROCESS FOR PRODUCING THE SAME

TECHNICAL FIELD

The present invention relates to polysaccharides containing phosphorylcholine groups and methods for manufacturing them.

The phosphorylcholine group-containing polysaccharide of the present invention is superior in biocompatibility and moisture retention, and is useful as a polymer material for medical use. Specifically, it is utilized in artificial organs, biomembranes, coating agents for medical tools, drug delivery, and in cosmetics.

BACKGROUND ART

Macromolecules containing phosphorylcholine groups have been developed as biocompatible materials. Polymers having phosphorylcholine groups have been synthesized mainly as follows: acryl type monomers mainly having hydroxyl groups and 2-chloro-1,3,2-dioxaphosphorane-2-oxide are brought into reaction and then trimethylamine is used to turn the reaction product into quaternary ammonium to synthesize monomers having a phosphorylcholine structure, which are then polymerized.

However, due to the monomer solubility issues when introducing the hydrophobic groups, this method requires the use of an organic solvent known as a chain transfer catalyst such as methanol, ethanol, and chloroform as a polymerization solvent, which makes it difficult to produce high molecular weight polymers. Also, the monomer synthesis reaction has to be conducted under strictly anhydrous conditions, which complicates the technique.

In addition the conventional manufacturing method that polymerizes monomers having phosphorylcholine on side chains has a problem in that the steric hindrance of the phosphorylcholine group reduces the polymerization yield or makes it impossible to obtain the desired polymer.

In view of the description above, the inventors conducted earnest research on the manufacturing method of the phosphorylcholine group-containing polymer, and completed the present invention by discovering that polysaccharides having the phosphorylcholine structure can be obtained easily and with a high versatility by reacting a compound containing phosphorylcholine groups with a polysaccharide having a functional group that reacts with this compound, which leads to a macromolecular reaction in the side chains of the polymer.

DISCLOSURE OF INVENTION

That is, the present invention provides a polysaccharide having a phosphorylcholine group represented by the following general formula (1).

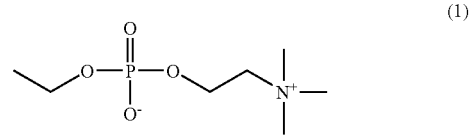

(1)

That is, the present invention provides a polysaccharide having a phosphorylcholine group represented by the following general formulas (2)-(10).

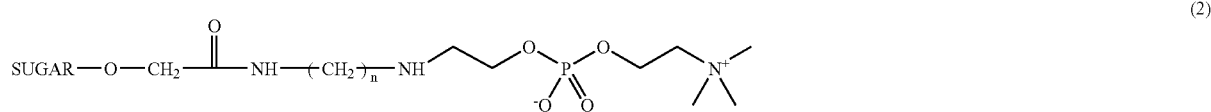

(2)

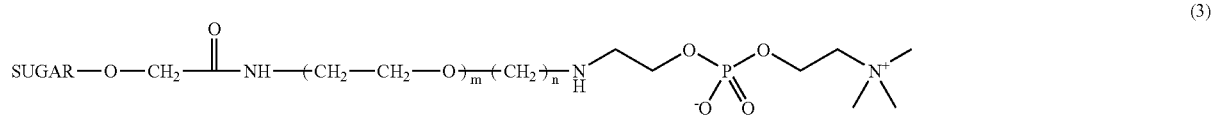

(3)

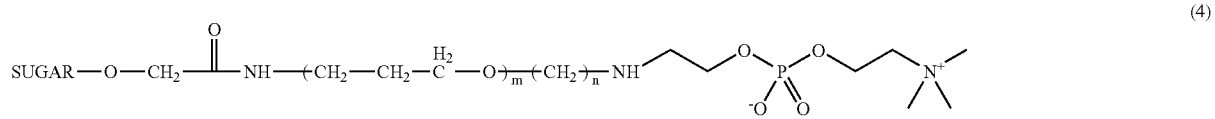

(4)

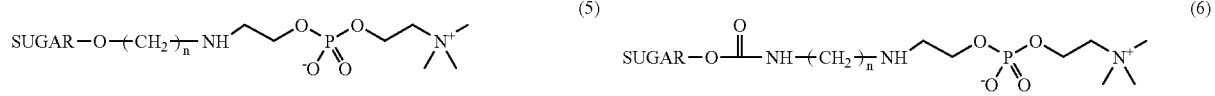

(5)

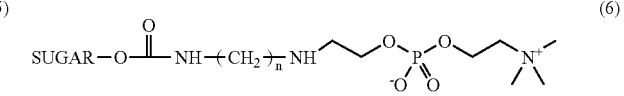

(6)

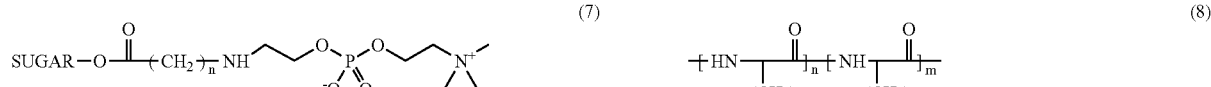

(7)

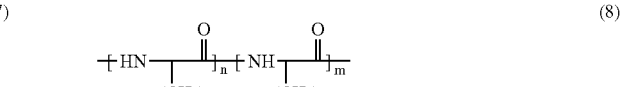

(8)

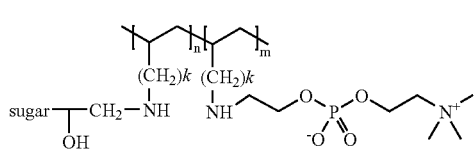 (9)

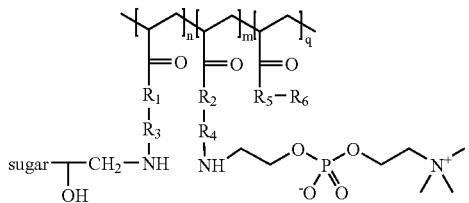 (10)

In the general formulas (2)-(7) n denotes an integer 1-22, m denotes an integer 1-20, and SUGAR denotes a polysaccharide.

In general formulas (8)-(10), R1, R2, and R5 denote O, NH, or a tertiary amine.

R3 and R4 are straight chain or branched alkylene having 1-22 carbon atoms, or ethylene oxide having 1-20 repeat units.

R6 denotes a hydrocarbon including aromatic hydrocarbons or a perfluoroalkylene group having 1-22 carbon atoms.

k denotes an integer 0-6, n, m, and q denote positive integers, and "sugar" denotes a polysaccharide.

Furthermore, the present invention provides a method for manufacturing a polysaccharide having phosphorylcholine groups wherein the aldehyde derivative-containing compound obtained by the oxidative ring-opening reaction of glycerophosphorylcholine is added to a polysaccharide containing amino groups.

BEST MODE FOR CARRYING OUT THE INVENTION

Figure 1:
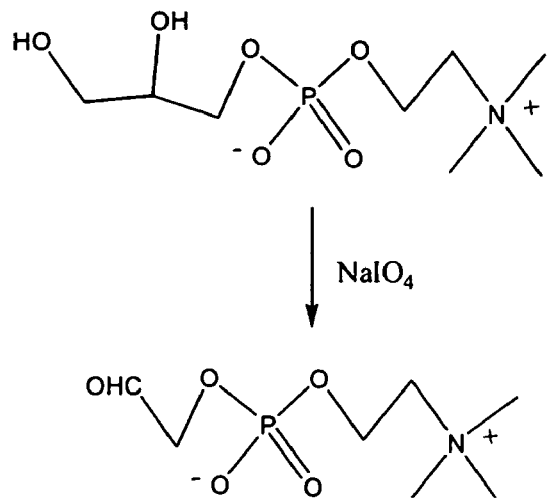
FIG. 1 shows a scheme for preparing a monofunctional aldehyde derivative containing a phosphorylcholine group.

The present invention is described in detail below.

The preparation method of the polysaccharide containing phosphorylcholine groups of the present invention is as follows.

[1]: A polysaccharide having amino groups is brought into a reductive amination reaction with a hydrate derivative or aldehyde derivative obtained by the oxidative ring-opening reaction of glycerophosphorylcholine to obtain a polysaccharide to which phosphorylcholine groups are added.

A polysaccharide having phosphorylcholine groups added to its main chain has not been reported. The only method known for such a polysaccharide uses graft polymerization to indirectly introduce phosphorylcholine groups to side chains away from the main chain (Journal of Biomedical Materials Research, Vol. 29, 181-188 (1995)), but this method has the shortcoming of being cumbersome.

The preparation method of the present invention using the reaction described in [1] has significant advantages in that the introduction yield is high and the introduction ratio can be controlled easily.

For example, the introduction ratio of phosphorylcholine can be controlled to change the hydrophilicity of the polymer or to adapt to required biocompatibility. Also, free from the influence of the phosphorylcholine groups, sugar chains can be given required functions by means of hydrophobic groups and such, and then any quantity of phosphorylcholine groups can be added to easily obtain the target functional polymer material. A form of polymer that introduces phosphorylcholine in the main chain of a polysaccharide, or a form of polymer that introduces phosphorylcholine into the main chain of the polymer introduced to a polysaccharide can be synthesized, allowing flexibility according to the application.

In the preparation method [1] in the present invention, the compound containing the aldehyde derivative obtained by the oxidative ring-opening reaction of glycerophosphorylcholine is obtained by oxidative ring-opening of the prior art glycerophosphorylcholine group by means of a prior art method, which is a very easy step.

This reaction uses periodic acid or periodate to oxidize 1,2-diol to open the bond and obtain two aldehyde derivatives; in this particular method, a phosphorylcholine aldehyde derivative and formaldehyde are produced. The reaction is usually carried out in water or in an organic solvent containing water. The reaction temperature is between 0° C. to room temperature. The aldehyde derivative may go through the equilibrium reaction in water to become a hydrate, but this does not affect the subsequent reaction with the amine.

Selection of the polysaccharide having amino groups is not limited in particular. It suffices if the side chains of the polysaccharide have amino groups with which the aldehyde derivative obtained by the oxidative ring-opening reaction of glycerophosphorylcholine can react.

Prior art polysaccharides can be used. A prior art method can be used to introduce amino groups into a prior art polysaccharide to obtain a polysaccharide tailored for a target application.

Examples of the polysaccharide include dextran, cellulose, hyaluronic acid, pullulan, glucomannan, chondroitin sulfate, agarose, pectin, chitin, chitosan, gum Arabic, carrageenan, gellan, guar gum, alginic acid, xanthan gum, amylose, and rheozan.

Amino groups can be added to the polysaccharide by, for example, introduction of carboxylic acid via the carboxymethylation reaction followed by the amidation reaction with diamine. A polysaccharide containing amino groups, such as chitosan, can be used for the phosphorylcholine introduction reaction without further treatment. The phosphorylcholine group content of the final target product can be designed by controlling the amino group content.

Amino group-containing polysaccharides can also be obtained by reductive amination coupling between common polysaccharides having reductive terminals and polymers having amino groups such as polylysine or polyethyleneimine.

The reductive amination reaction for bonding the aldehyde derivative (or hydrate derivative polymer) obtained by the oxidative ring-opening reaction of glycerophosphorylcholine to the amino groups of the polymer can be carried out easily by stirring both of them in a solvent.

This reaction is carried out by dissolving those two in water or alcohol (a third organic solvent ingredient can be mixed in, too) to form an imine and reducing it with a reducing agent to obtain a secondary amine.

For the reducing agent, a mild reducing agent such as sodium cyanoboronate is preferable, but other reducing agents can be used as long as the phosphorylcholine is stable. The reaction is usually carried out at 0° C. to room temperature, but heating may be done depending on the situation.

Using the aforementioned preparation method, a polysaccharide containing a desired amount of phosphorylcholine groups in the hydrophilic portion is easily obtained.

It is also possible to design a biocompatible polymer having the structure of biomembrane components such as phosphatidylethanolamine, phosphatidylserine, phosphatidylinositol, and diphosphatidylglycerol.

The hydrophilic portion of the polysaccharide may include a carboxylate group, hydroxyl group, primary-tertiary amine group, sulfonate group, phosphate group, polyoxyethylene group, ammonium group, amide, carboxybetaine, and saccharide, and the type and content of these in the polysaccharide can be adjusted to design its functions.

As for the hydrophobic portion of the polysaccharide, depending on the application, straight chain or branched alkyls having 1-22 carbon atoms, cyclic alkyls such as cholesterol, alkyl groups containing unsaturated bonds such as oleyl, hydrocarbon type aromatics such as benzene rings, naphthalene rings, and pyrene, hetero type aromatics such as pyridine rings, imidazole, thiazole, and indole, and hydrophobic groups such as perfluoroalkyl and polyalkylsiloxane can be introduced for molecular design.

The hydrophobic group can bond directly to the main chain with the ester, ether, amide, urethane, or urea bond, or indirectly via a spacer. Examples of the spacer include hydrophilic polyethyleneoxide, hydrophobic polypropyleneoxide, and straight chain alkyls having 2-22 carbon atoms.

Using the aforementioned preparation method, the polysaccharides of the present invention represented in general formulas (1)-(10) can easily be prepared.

The polysaccharides represented by general formulas (2)-(10) have the characteristic of having a polysaccharide and phosphorylcholine bonded via a secondary amine. Phosphorylcholine directly bonds to the polymer main chain via a secondary amine.

The preparation method of the present invention can be used to bond a polysaccharide and phosphorylcholine via a secondary amine and also to bond phosphorylcholine in the polymer prepared by bonding an acrylic polymer and such to sugar terminals in the block fashion.

The polysaccharide having phosphorylcholine groups of the present invention is a polysaccharide polymer material with superior hydrophilicity and moisture retention.

In general formulas (2)-(10), "sugar", which represents a polysaccharide, can contain hetero-aromatic groups, aromatic groups, perfluoroalkyl groups, and straight chain or branched alkyl groups having 1-22 carbon atoms.

The polysaccharides of general formulas (8)-(10) are polymers composed of phosphorylcholine groups and polysaccharides added to polymer main chains.

Such a polymer is the result of the addition of polysaccharide and phosphorylcholine groups via amino groups; it is a polymer containing two or three types of repeat units represented by parentheses followed by m, n, or q; usually, the repeat units to which the polysaccharide and phosphorylcholine groups are added are randomly polymerized. m, n, and q are positive integers; they indicate the composition of the polymer in terms of the repeat units to which the polysaccharide and phosphorylcholine groups, respectively, are added.

Since preparation is done by the polymer reaction in which the polysaccharide and the phosphorylcholine groups are added to a polymer having amino groups, the polymer can contain repeat units in which amino groups remain to which no polysaccharide or phosphorylcholine groups are added.

Selection of the polysaccharide in general formulas (2)-(7) is not limited in particular; any polysaccharide having hydroxyl groups and soluble in the reaction solvent can be used.

Selection of the polysaccharide in general formulas (8)-(10) is not limited in particular; any polysaccharide having reductive terminals and soluble in the reaction solvent can be used.

The polysaccharides having phosphorylcholine groups in general formulas (2)-(10) can be easily prepared from the polysaccharides containing amino groups represented by the following general formulas (11)-(19) by means of the preparation method of the present invention. Other than these general formulas, sugar that naturally has amino groups (such as chitosan) can be used.

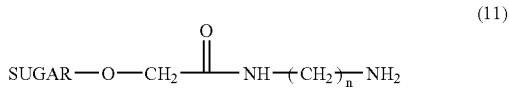

(11)

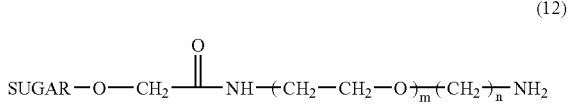

(12)

-continued

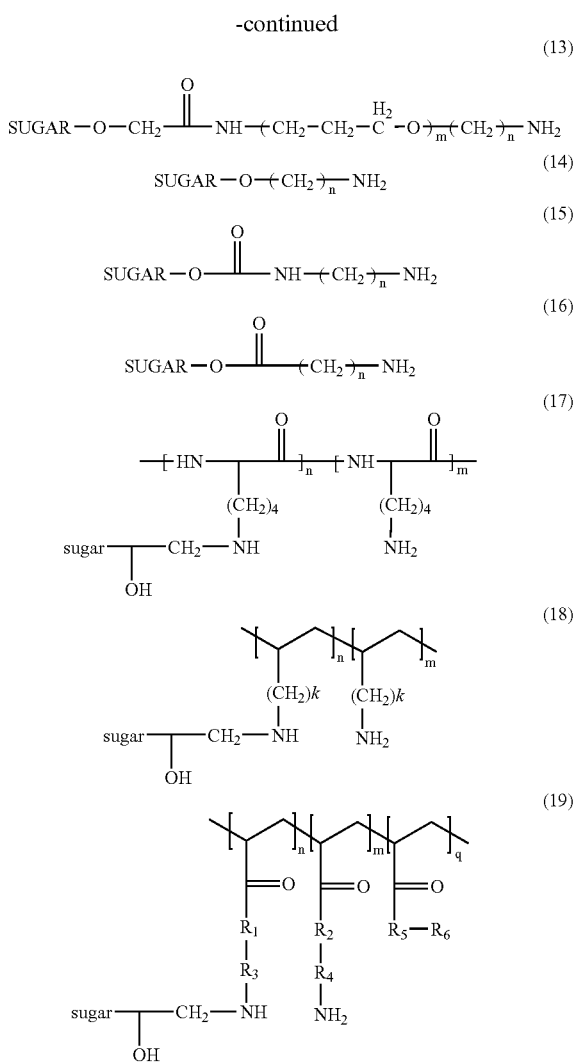

In the general formulas (11)-(16) n denotes an integer 1-22, m denotes an integer 1-20, and SUGAR denotes a polysaccharide.

In general formulas (17)-(19), R1, R2, and R5 denote O, NH, or a tertiary amine.

R3 and R4 are straight chain or branched alkylenes having 1-22 carbon atoms, or ethylene oxide having 1-20 repeat units.

R6 denotes a hydrocarbon including aromatic hydrocarbons or a perfluoroalkylene group having 1-22 carbon atoms.

k denotes an integer 0-6, n, m, and q denote positive integers, and "sugar" denotes a polysaccharide.

Figure 2:
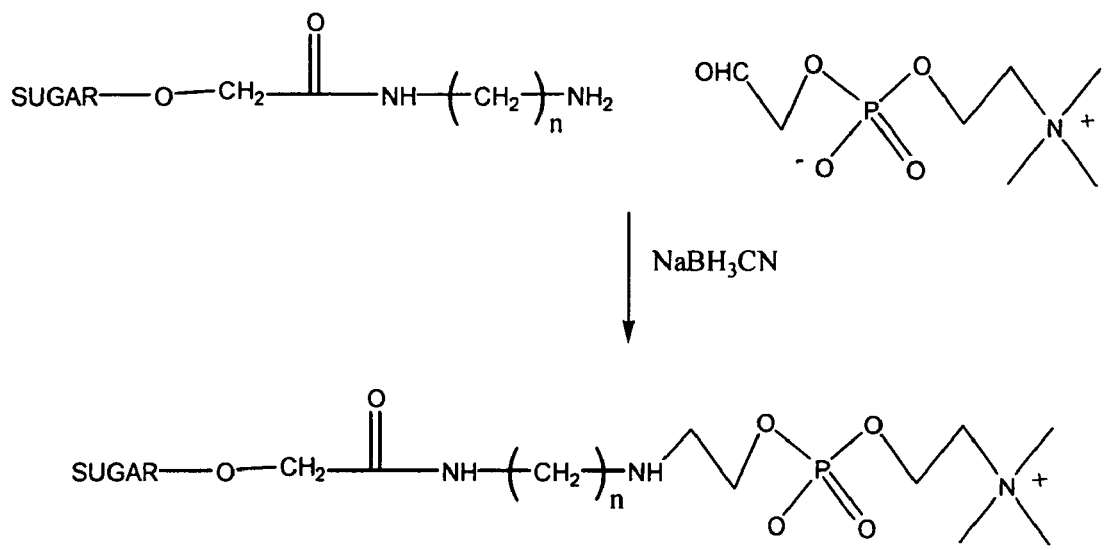
FIG. 2 shows a preparation scheme for the polysaccharide represented by general formula (2).

FIG. 1 shows a scheme for preparing a monofunctional aldehyde derivative containing a phosphorylcholine group, and FIG. 2 shows a preparation scheme for the polysaccharide represented by general formula (2).

These show that the target phosphorylcholine group-containing polysaccharide of the present invention can be easily obtained from the monofunctional phosphorylcholine aldehyde derivative by using the manufacturing method of the present invention.

The polysaccharides of general formulas (3)-(11) can also be obtained in the same manner.

EXAMPLES

Specific synthesis examples follow. The present invention is not limited to the following synthesis examples.

The composition of the polysaccharides of the present invention can be determined by NMR.

Synthesis Example 1

An aldehyde derivative containing a phosphorylcholine group

L-α-glycerophosphorylcholine (450 mg) is dissolved in 15 ml of distilled water and cooled in an ice water bath. Sodium periodate (750 mg) is added and two hours of stirring is carried out. Furthermore, ethylene glycol (150 mg) is added and overnightstirring is carried out. The reaction solution is vacuum-concentrated and vacuum-dried and the target substance is extracted with methanol.

Figure 3:
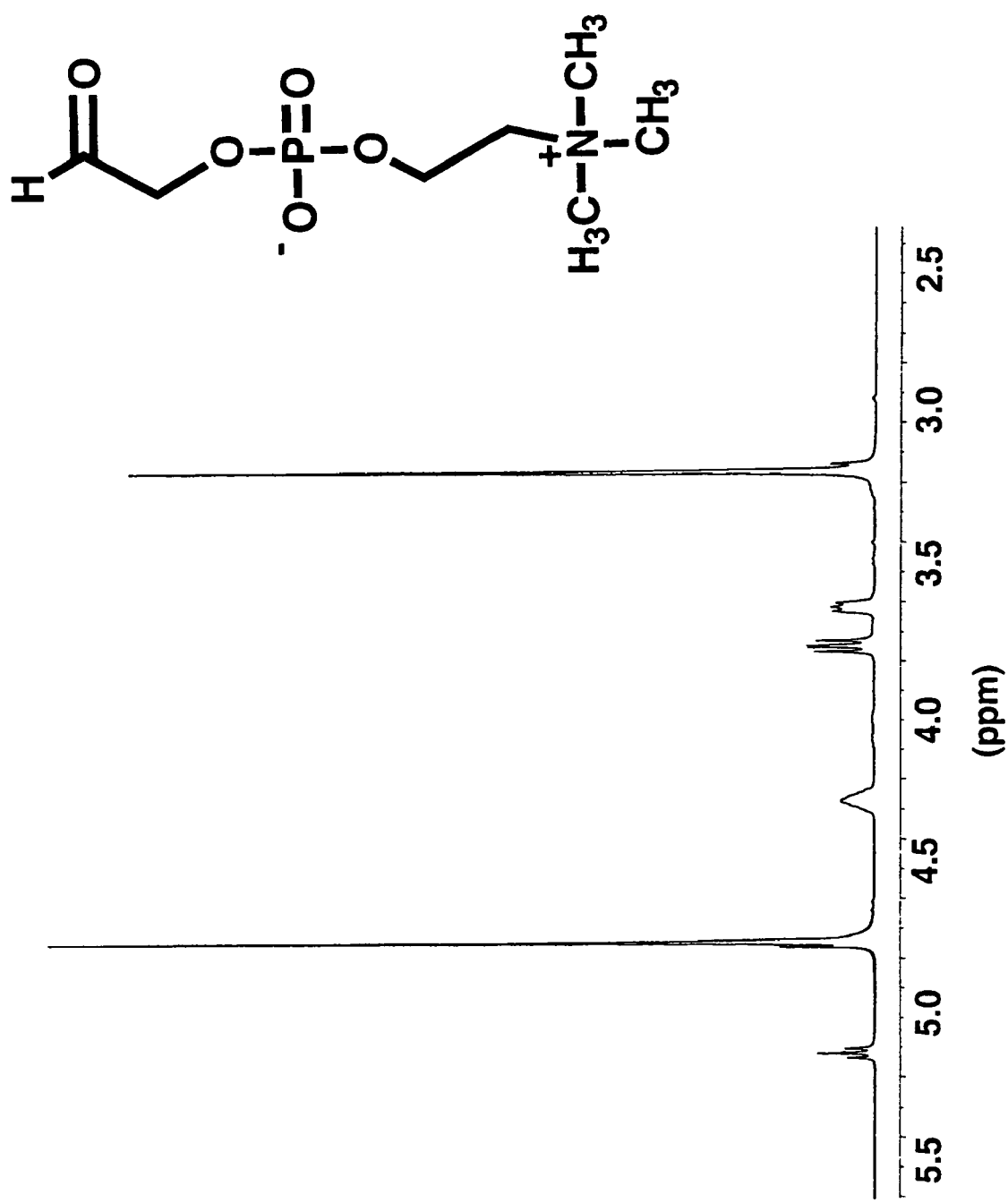
FIG. 3 shows a structural formula and NMR spectrum of synthesis example 1.

The structural formula and the NMR spectrum are shown in FIG. 3.

Synthesis Example 2

Synthesis of carboxymethyldextran

Dextran (5 g) and chloroacetic acid (10.28 g) are dissolved in a 6N solution of sodium hydrochloride, followed by heating and stirring for one hour at 60° C. After cooling the mixture down to room temperature, the target substance is obtained by means of reprecipitation in methanol. (Yield 6.2 g).

Figure 4:
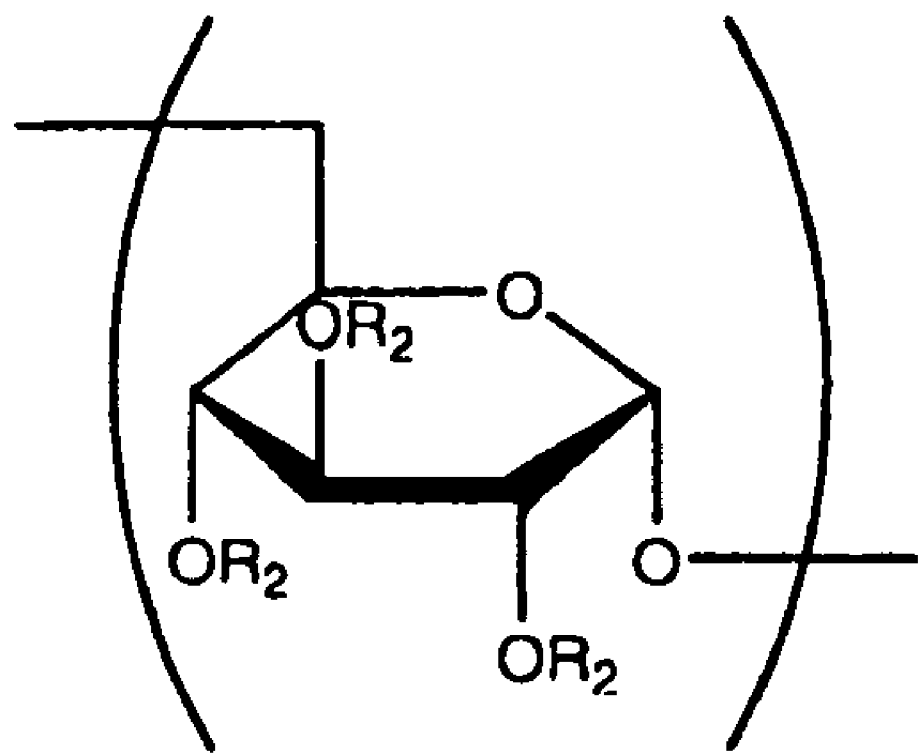
FIG. 4 is a structural formula of synthesis example 2.
Figure 4:
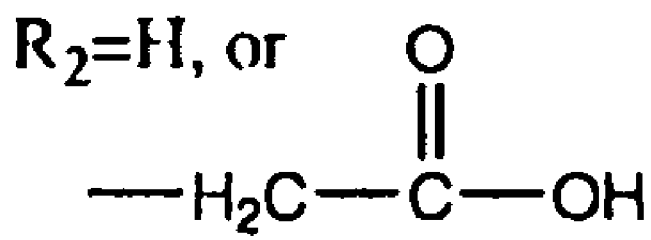

The structural formula is shown in FIG. 4.

Synthesis Example 3

Synthesis of aminodextran

The carboxydextran (1 g) of Synthesis example 2 and ethyelenediamine (10 ml) are dissolved in distilled water (10 ml) and the pH is adjusted to five. 1{3-(dimethylamino)propyl}3-ethylcarbodiimide hydrochloride (1.5 g) is gradually added. After stirring overnight at room temperature, the reaction solution is dialyzed in water and 1.25 g of the target substance is obtained by means of lyophilization.

Figure 5:
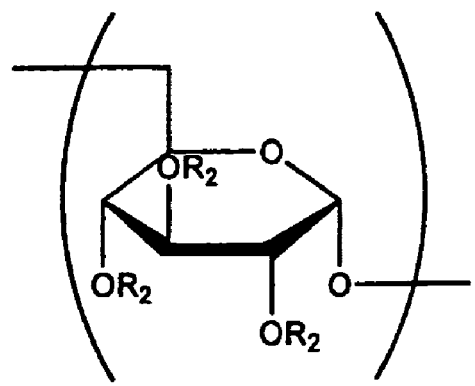
FIG. 5 shows a structural formula and NMR spectrum of synthesis example 3.
Figure 5:
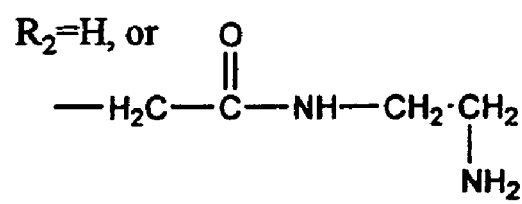
Figure 5:
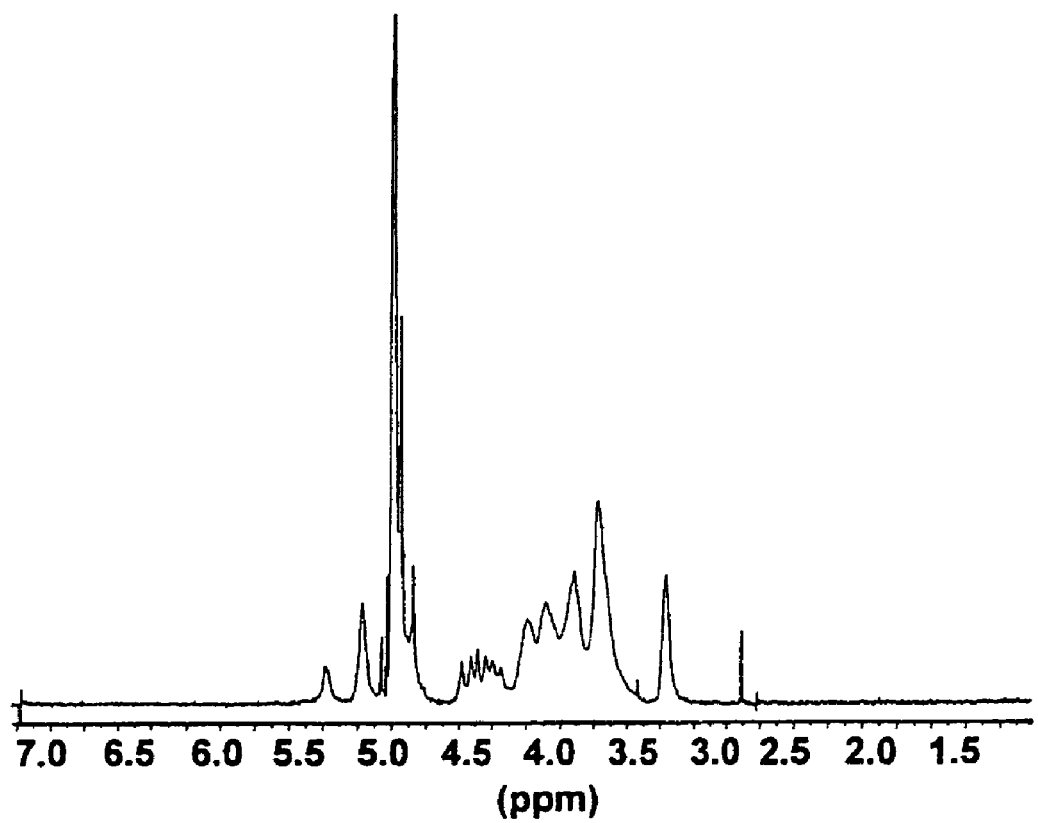

The structural formula and the NMR spectrum are shown in FIG. 5.

Synthesis Example 4

Synthesis of aminocellulose

Carboxymethylcellulose (1 g) and ethyelenediamine (10 ml) are dissolved in distilled water (10 ml) and the pH is adjusted to five. 1{3-(dimethylamino)propyl}3-ethylcarbodiimide hydrochloride (1.5 g) is gradually added. After stirring overnight at room temperature, the reaction solution is dialyzed in water and 1.05 g of the target substance is obtained by means of lyophilization.

Figure 6:
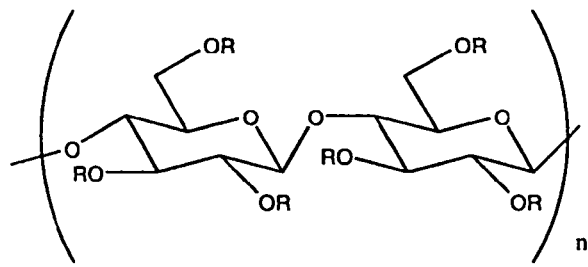
FIG. 6 shows a structural formula and NMR spectrum of synthesis example 4.

The structural formula and the NMR spectrum are shown in FIG. 6.

Synthesis Example 5

Synthesis of aminohyaluronic acid

Hyaluronic acid (1 g) and ethyelenediamine (10 ml) are dissolved in distilled water (10 ml) and the pH is adjusted to five.

1{3-(dimethylamino)propyl}3-ethylcarbodiimide hydrochloride (1.5 g) is gradually added. After stirring overnight at room temperature, the reaction solution is dialyzed in water and 1.2 g of the target substance is obtained by means of lyophilization.

Figure 7:
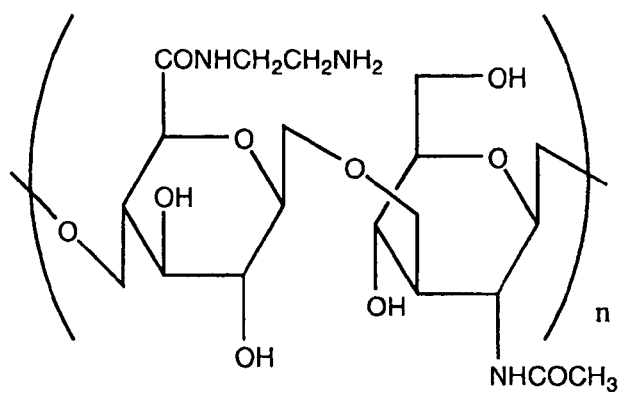
FIG. 7 is a structural formula of synthesis example 5.

The structural formula is shown in FIG. 7.

Synthesis Example 6

Synthesis of carboxymethylpullulan

Pullulan (5 g) and chloroacetic acid (10.28 g) are dissolved in a 6N sodium hydrochloride solution, followed by one hour of heating and stirring at 60° C. After cooling the mixture down to room temperature, the target substance is obtained by means of reprecipitation in methanol. (Yield 5.1 g).

Figure 8:
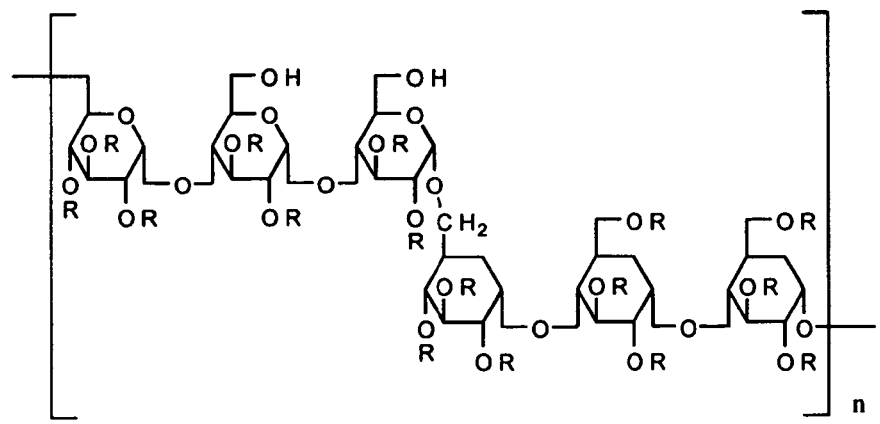
FIG. 8 is a structural formula of synthesis example 6.

The structural formula is shown in FIG. 8.

Synthesis Example 7

Synthesis of aminopullulan

The carboxypullulan (1 g) of Synthesis example 6 and ethyelenediamine (10 ml) are dissolved in distilled water (10 ml) and the pH is adjusted to five. 1{3-(dimethylamino) propyl}3-ethylcarbodiimide hydrochloride (1.5 g) is gradually added. After stirring overnight at room temperature, the reaction solution is dialyzed in water and 1.15 g of the target substance is obtained by means of lyophilization.

Figure 9:
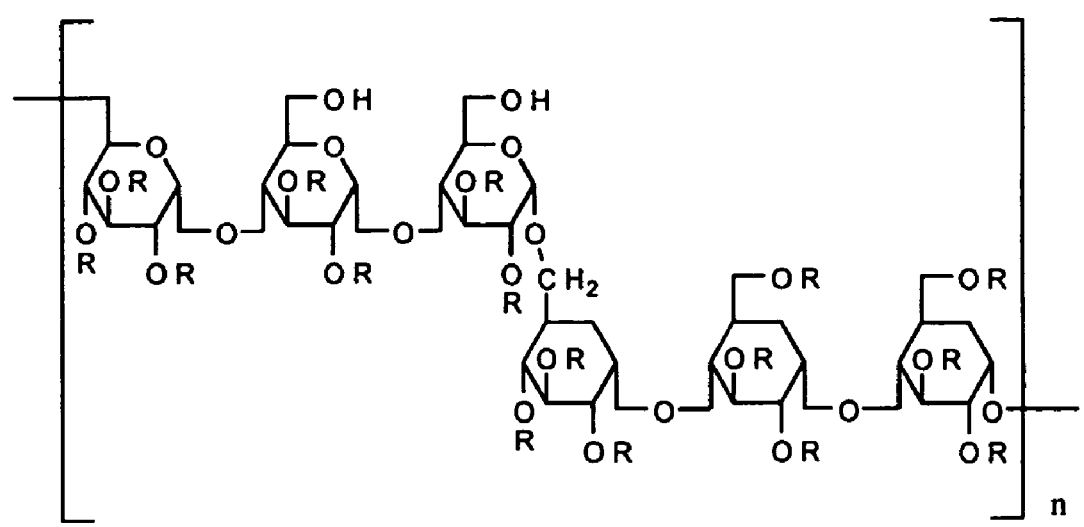
FIG. 9 is a structural formula of synthesis example 7.

The structural formula is shown in FIG. 9.

Synthesis Example 8

Synthesis of phosphorylcholinedextran

The phosphorylcholine aldehyde (1 g) of Synthesis example 1 is added to the aminodextran (1 g) solution (15 ml) of Synthesis example 3, followed by stirring for five hours at room temperature. Sodium cyanoborate hydride (500 mg) is added, followed by overnight stirring. The target substance (1.1 g) is obtained after purification by means of dialyzation and lyophilization.

Figure 10:
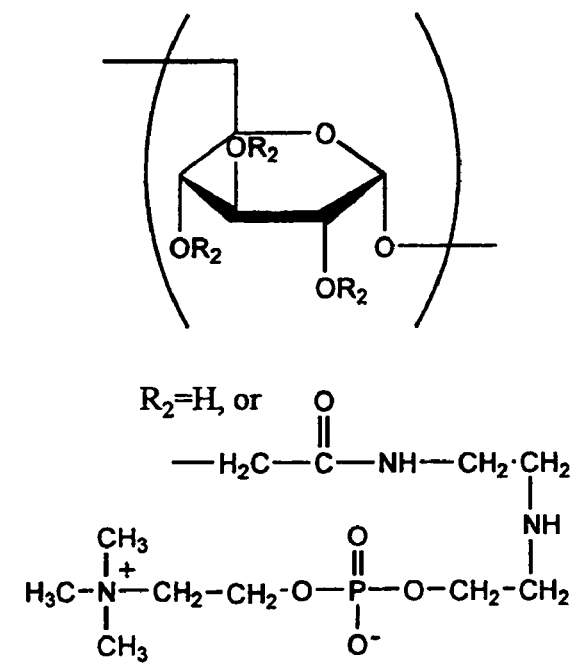
FIG. 10 shows a structural formula and NMR spectrum of synthesis example 8.
Figure 10:
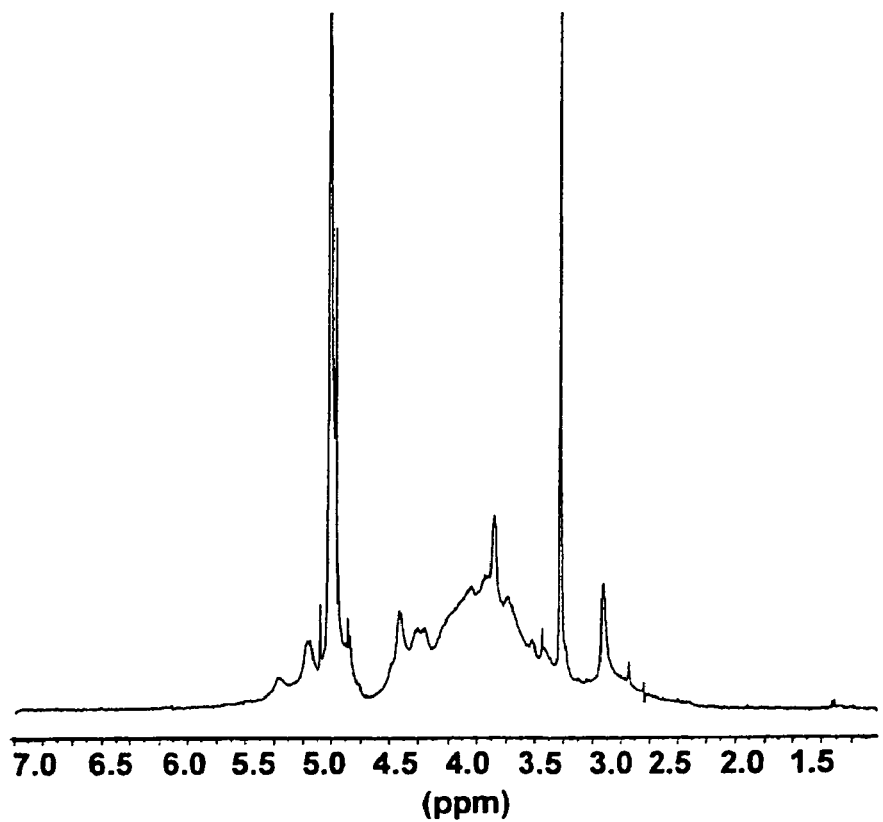

The structural formula and the NMR spectrum are shown in FIG. 10.

Synthesis Example 9

Synthesis of phosphorylcholinecellulose

The phosphorylcholine aldehyde (1 g) of Synthesis example 1 is added to the aminocellulose (1 g) solution (15 ml) of Synthesis example 4, followed by stirring for five hours at room temperature. Sodium cyanoborate hydride (500 mg) is added, followed by overnight stirring. The target substance (1.05 g) is obtained after purification by means of dialyzation and lyophilization.

Figure 11:
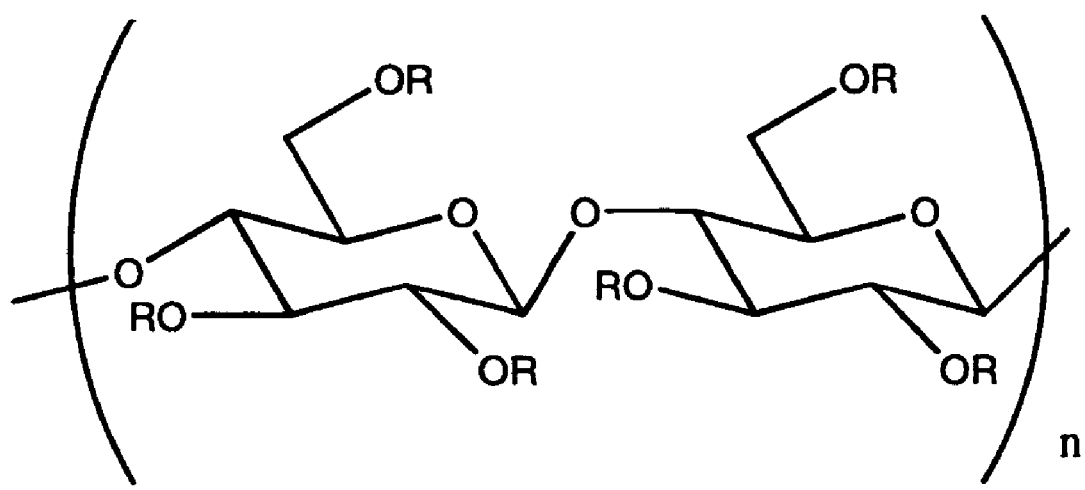
FIG. 11 is a structural formula of synthesis example 9.
Figure 11:
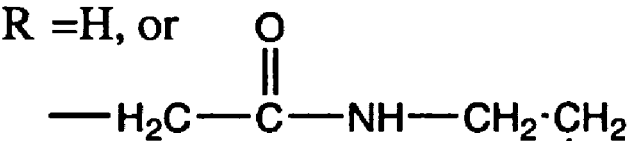
Figure 11:
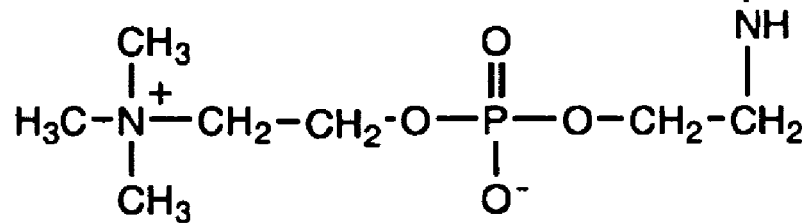

The structural formula is shown in FIG. 11.

Synthesis Example

Synthesis of phosphorylcholinehyaluronic acid

The phosphorylcholine aldehyde (1 g) of Synthesis example 1 is added to the aminohyaluronic acid (1 g) solution (15 ml) of Synthesis example 6, followed by stirring for five hours at room temperature. Sodium cyanoborate hydride (500 mg) is added, followed by overnight stirring. The target substance (1.2 g) is obtained after purification by means of dialyzation and lyophilization.

Figure 12:
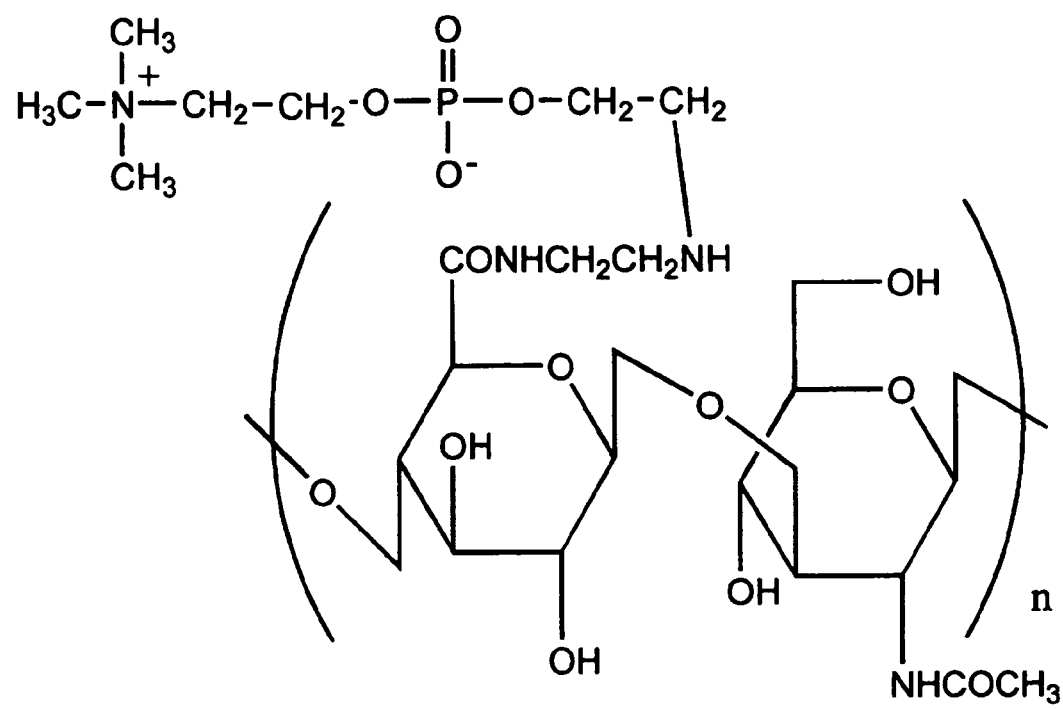
FIG. 12 shows a structural formula and NMR spectrum of synthesis example 10.
Figure 12:
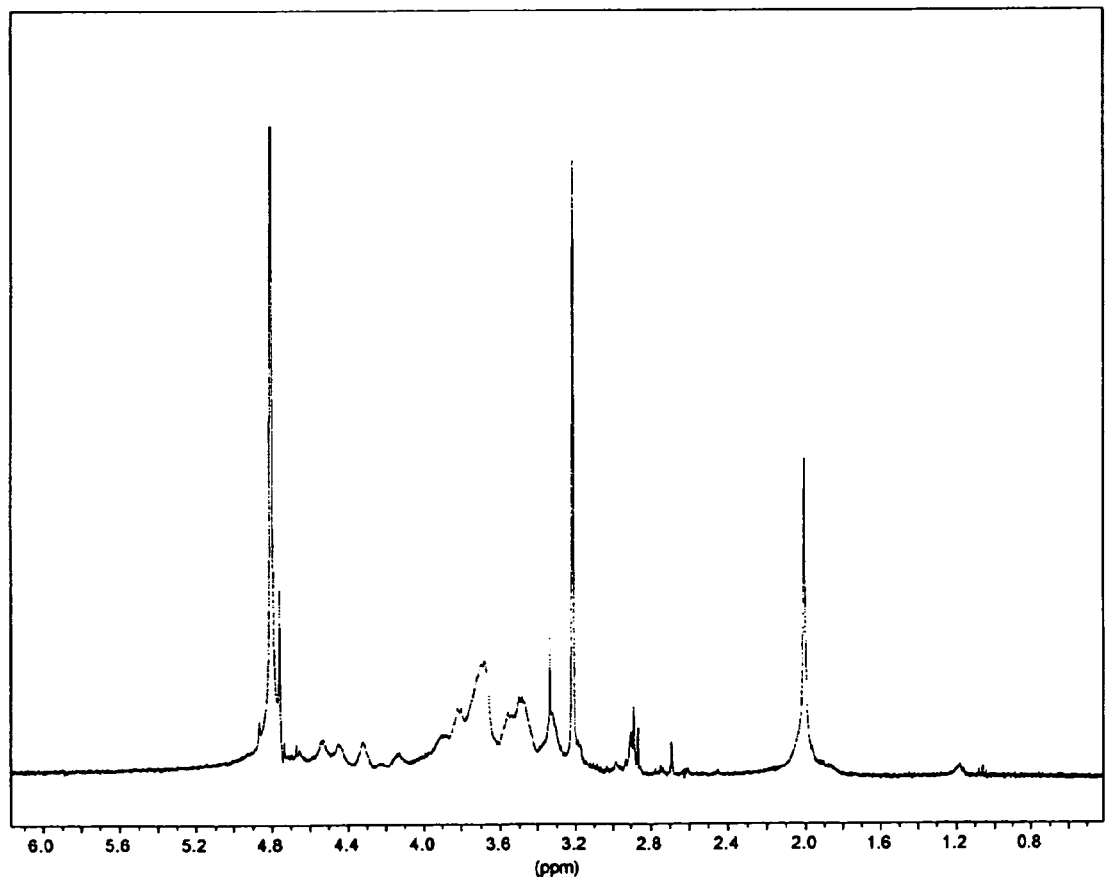

The structural formula and the NMR spectrum are shown in FIG. 12.

Synthesis Example

Synthesis of phosphorylcholinepullulan

The phosphorylcholine aldehyde (1 g) of Synthesis example 1 is added to the aminopullulan (1 g) solution (15 ml) of Synthesis example 8, followed by stirring for five hours at room temperature. Sodium cyanoborate hydride (500 mg) is added, followed by overnight stirring. The target substance (0.99 g) is obtained after purification by means of dialyzation and lyophilization.

Figure 13:
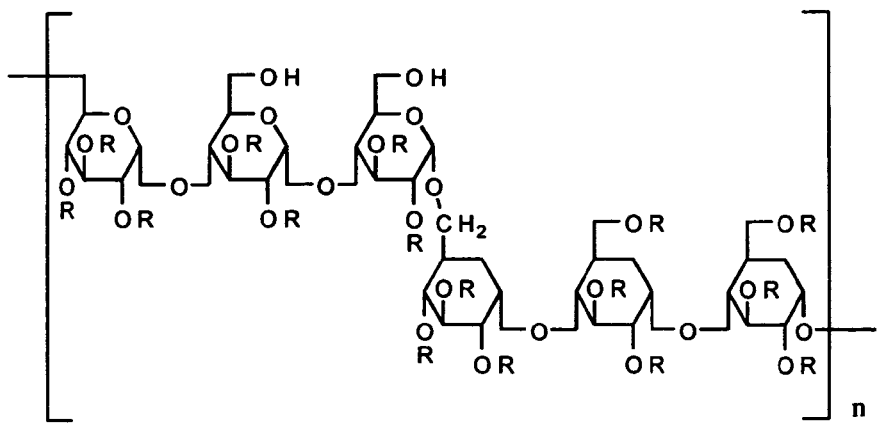
FIG. 13 is a structural formula of synthesis example 11.
Figure 13:
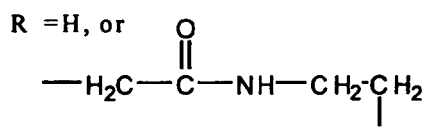
Figure 13:
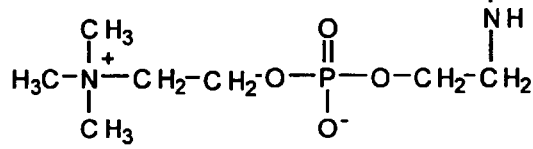

The structural formula is shown in FIG. 13.

Synthesis Example

Synthesis of hydrophobicized phosphorylcholinedextran

A DMF solution (15 ml) of lauric acid (0.02 g) is added to the aminodextran (1 g) solution (15 ml) of Synthesis example 3, and 1{3-(dimethylamino)propyl}3-ethylcarbodiimide hydrochloride (1.5 g) is gradually added. After stirring overnight at room temperature, the reaction solution is dialyzed in water, and the phosphorylcholine aldehyde (1 g) of Synthesis example 1 is added to this aqueous solution, followed by stirring for five hours at room temperature. Sodium cyanoborate hydride (500 mg) is added, followed by overnight stirring. The target substance (1.1 g) is obtained after purification by means of dialyzation and lyophilization.

Figure 14:
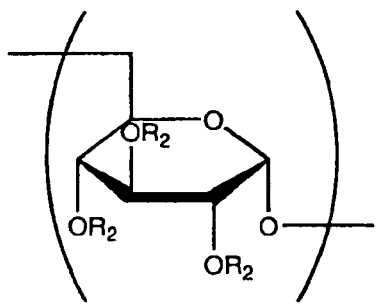
FIG. 14 is a structural formula of synthesis example 12.
Figure 14:
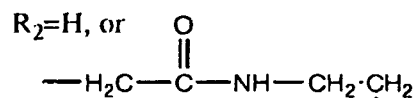
Figure 14:
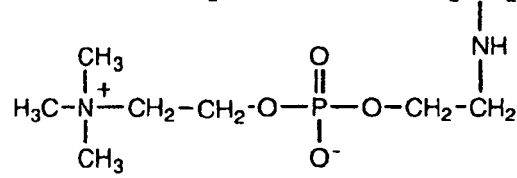

The structural formula is shown in FIG. 14.

Synthesis Example 13

Synthesis of hydrophobicized phosphorylcholinecellulose

A DMF solution (15 ml) of stearic acid (0.01 g) is added to the aminodextran (1 g) solution (15 ml) of Synthesis example 4, and 1{3-(dimethylamino)propyl}3-ethylcarbodiimide hydrochloride (1.5 g) is gradually added. After stirring overnight at room temperature, the reaction solution is dialyzed in water, and the phosphorylcholine aldehyde (1 g) of Synthesis example 1 is added to this aqueous solution, followed by stirring for five hours at room temperature. Sodium cyanoborate hydride (500 mg) is added, followed by overnight stirring. The target substance (0.89 g) is obtained after purification by means of dialyzation and lyophilization.

Figure 15:
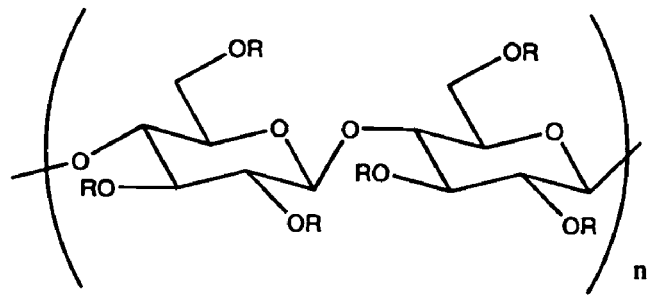
FIG. 15 is a structural formula of synthesis example 13.
Figure 15:
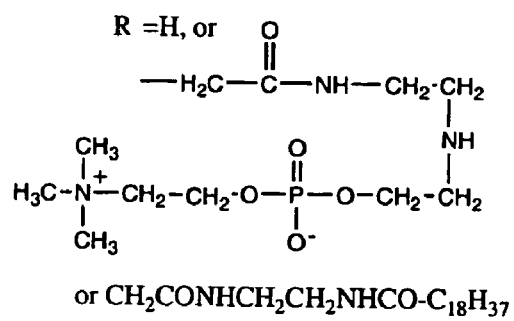

The structural formula is shown in FIG. 15.

Synthesis Example

Synthesis of hydrophobicized phosphorylcholinehyaluronic acid

A DMF solution (15 ml) of perfluorooctanoic acid (0.2 g) is added to the aminohyaluronic acid (1 g) aqueous solution (15 ml) of Synthesis example 5, and 1{3-(dimethylamino) propyl}3-ethylcarbodiimide hydrochloride (1.5 g) is gradually added. After stirring overnight at room temperature, the reaction solution is dialyzed in water, and the phosphorylcholine aldehyde (1 g) of Synthesis example 1 is added to this aqueous solution, followed by stirring for five hours at room temperature. Sodium cyanoborate hydride (500 mg) is added, followed by overnight stirring. The target substance (1.2 g) is obtained after purification by means of dialyzation and lyophilization.

Figure 16:
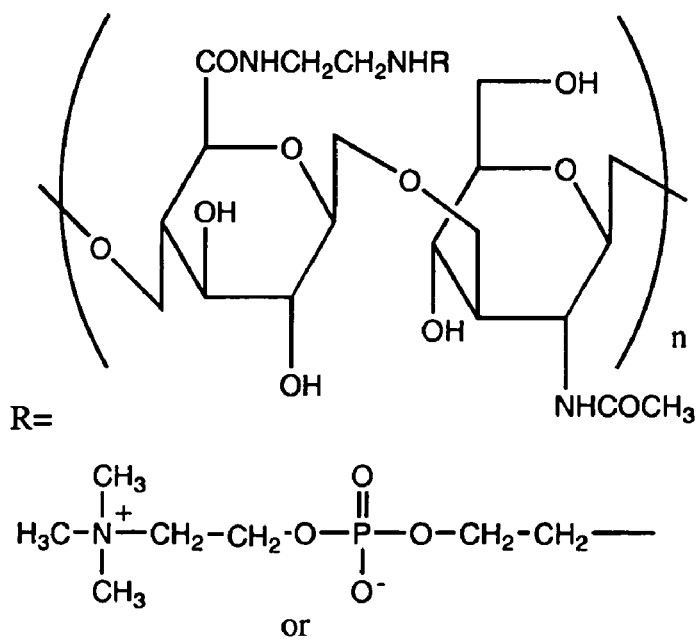
FIG. 16 is a structural formula of synthesis example 14.

The structural formula is shown in FIG. 16.

Synthesis Example 15

Synthesis of hydrophobicized phosphorylcholinepllulan

A DMF solution (15 ml) of lauric acid (0.02 g) is added to the aminopullulan (1 g) aqueous solution (15 ml) of Synthesis example 7, and 1{3-(dimethylamino)propyl}3-ethylcarbodiimide hydrochloride (1.5 g) is gradually added. After stirring overnight at room temperature, the reaction solution is dialyzed in water, and the phosphorylcholine aldehyde (1 g) of Synthesis example 1 is added to this aqueous solution, followed by stirring for five hours at room temperature. Sodium cyanoborate hydride (500 mg) is added, followed by overnight stirring. The target substance (1.1 g) is obtained after purification by means of dialyzation and lyophilization.

Figure 17:
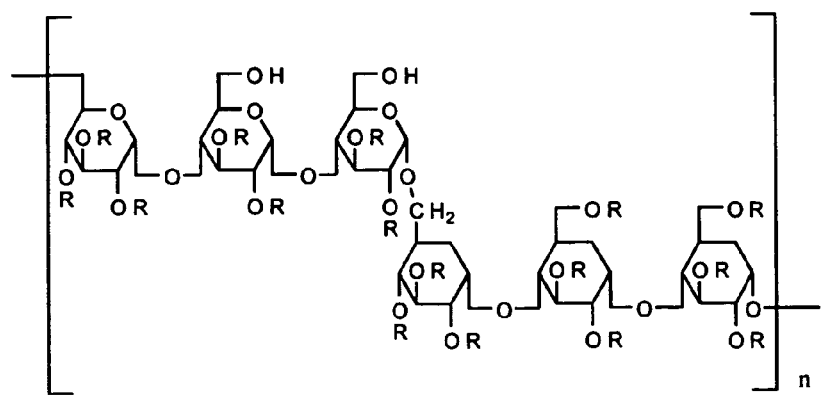
FIG. 17 is a structural formula of synthesis example 15.
Figure 17:
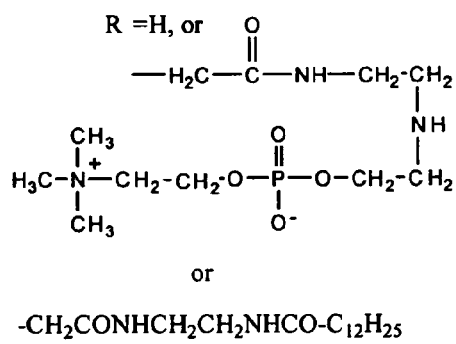

The structural formula is shown in FIG. 17.

Synthesis Example 16

Synthesis of hyaluronic acid-polylysine

Hyaluronic acid (1 g) and polylysine (1 g) are dissolved in distilled water (15 ml) and stirred at room temperature for five hours. Sodium cyanoborate hydride (500 mg) is added, followed by overnight stirring. The target substance (1.85 g) is obtained after purification by means of dialyzation and lyophilization.

Figure 18:
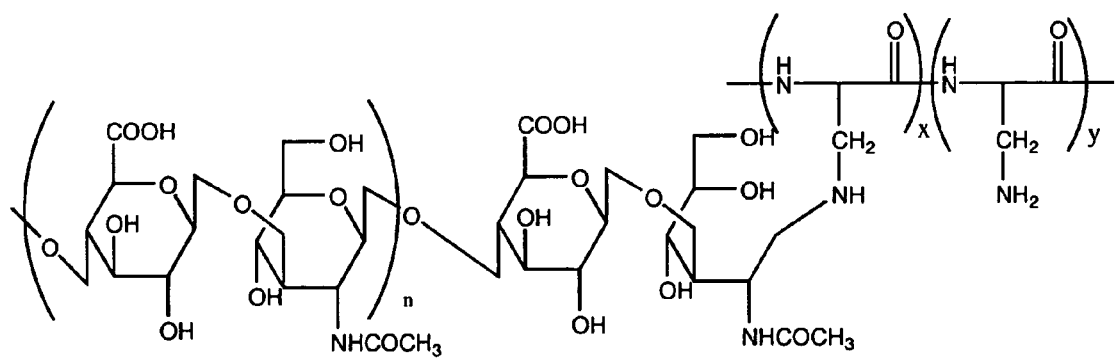
FIG. 18 is a structural formula of synthesis example 16.

The structural formula is shown in FIG. 18.

Synthesis Example

Synthesis of dextran-polyallylamine

Dextran (1 g) and polyallylamine (1 g) are dissolved in distilled water (15 ml) and stirred at room temperature for five hours. Sodium cyanoborate hydride (500 mg) is added, followed by overnight stirring. The target substance (1.6 g) is obtained after purification by means of dialyzation and lyophilization.

Figure 19:
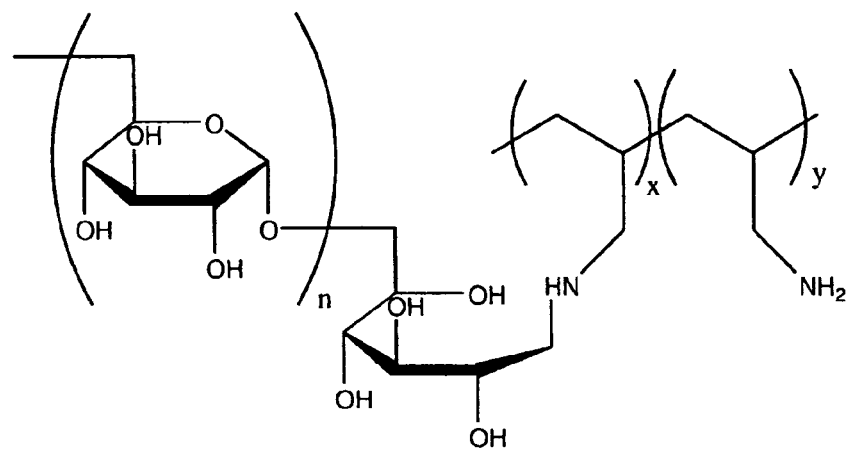
FIG. 19 is a structural formula of synthesis example 17.

The structural formula is shown in FIG. 19.

Synthesis Example 18

Synthesis of hydroxyethylcellulose-poly N-isopropylacrylamide-poly

N-(3-aminopropyl)methacrylamide Hydroxyethylcellulose (1 g) and hydroxyethylcellulose-poly N-isopropylacrylamide-poly N-(3-aminopropyl)methacrylamide 1:1 copolymer (1 g) are dissolved in distilled water (15 ml) and stirred at room temperature for five hours. Sodium cyanoborate hydride (500 mg) is added, followed by overnight stirring. The target substance (1.5 g) is obtained after purification by means of dialyzation and lyophilization.

Figure 20:
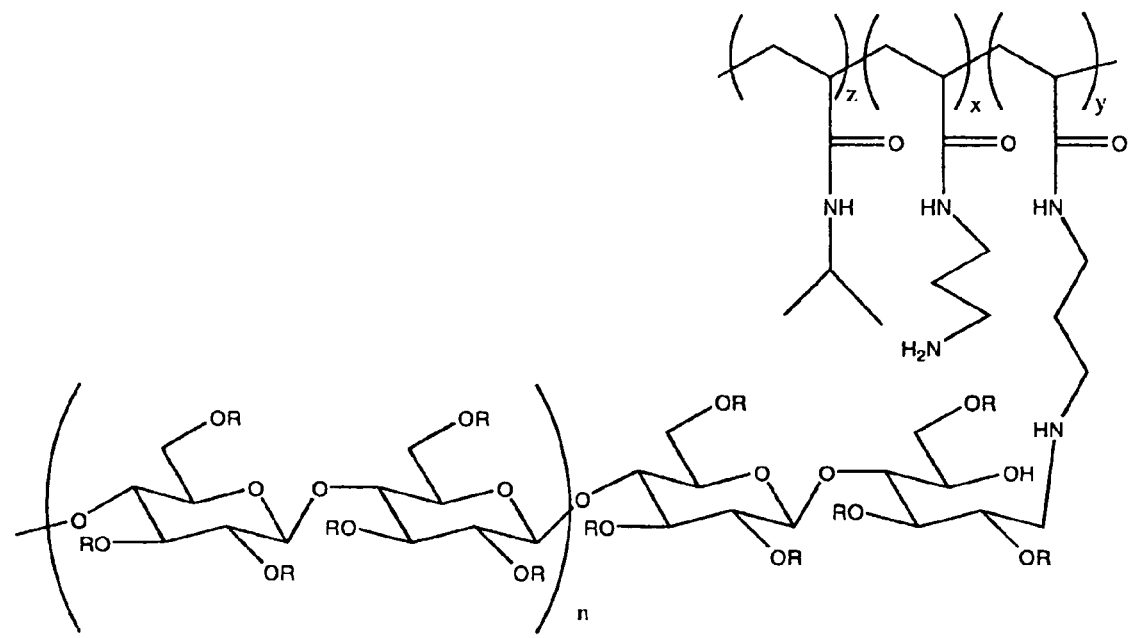
FIG. 20 is a structural formula of synthesis example 18.

The structural formula is shown in FIG. 20.

Synthesis Example 19

Synthesis of Hyaluronic acid-phosphorylcholinepolylysine

The phosphorylcholine aldehyde (1 g) of Synthesis example 1 is added to the hyaluronic acid-polylysine (1 g) aqueous solution (15 ml) of Synthesis example 17, followed by stirring for five hours at room temperature. Sodium cyanoborate hydride (500 mg) is added, followed by overnight stirring. The target substance (1.0 g) is obtained after purification by means of dialyzation and lyophilization.

Figure 21:
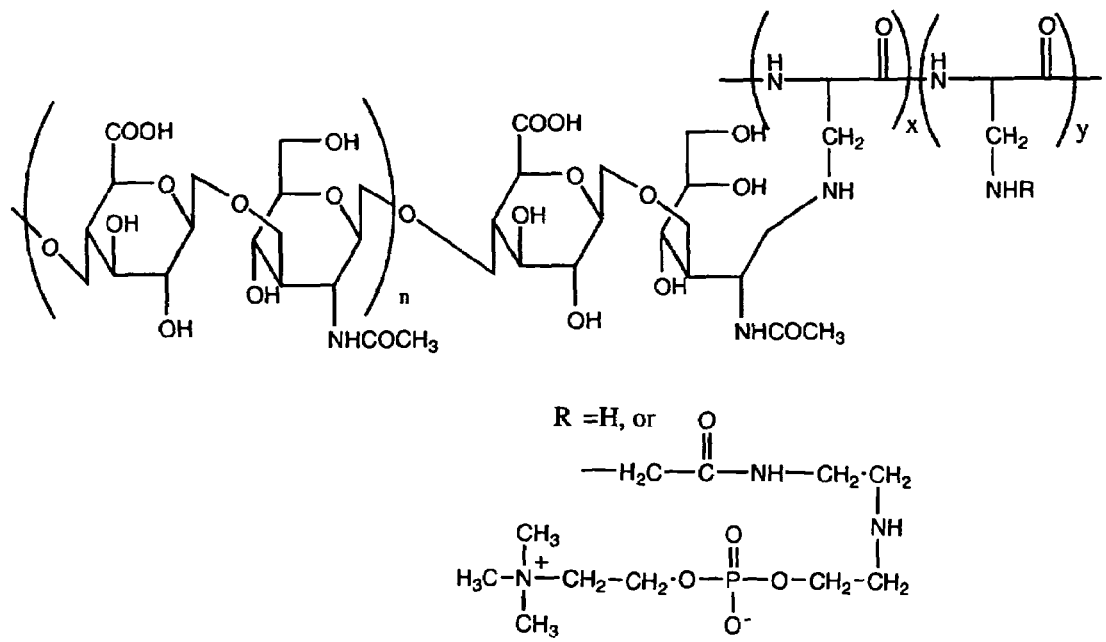
FIG. 21 is a structural formula of synthesis example 19.

The structural formula is shown in FIG. 21.

Synthesis Example 20

Synthesis of dextran-phosphorylcholinepolyallylamine

The phosphorylcholine aldehyde (1 g) of Synthesis example 1 is added to the polyallylamine (1 g) aqueous solution (15 ml) of Synthesis example 18, followed by stirring for five hours at room temperature. Sodium cyanoborate hydride (500 mg) is added, followed by overnight stirring. The target substance (1.2 g) is obtained after purification by means of dialyzation and lyophilization.

Figure 22:
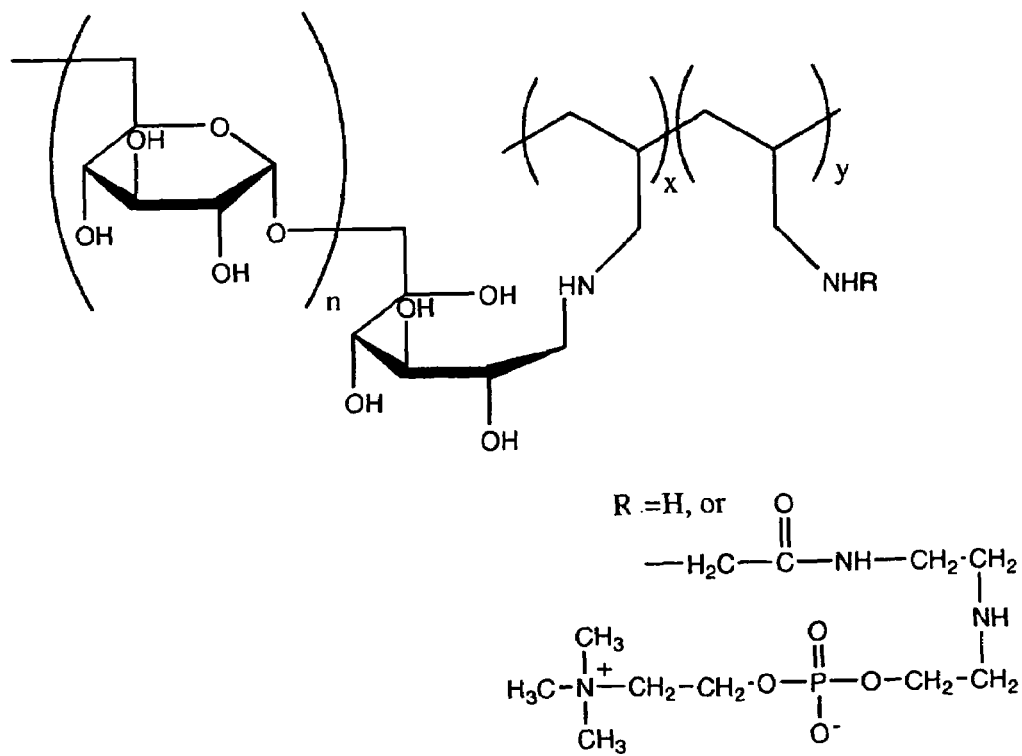
FIG. 22 is a structural formula of synthesis example 20.

The structural formula is shown in FIG. 22.

Synthesis Example 21

Synthesis of hydroxyethylcellulose-phosphorylcholine poly N-isopropylacrylamide-poly N-(3-aminopropyl)methacrylamide The phosphorylcholine aldehyde (1 g) of Synthesis example 1 is added to the hydroxyethylcellulose-poly N-isopropylacrylamide-poly N-(3-aminopropyl)methacrylamide (1 g) aqueous solution (15 ml) of Synthesis example 19, followed by stirring for five hours at room temperature. Sodium cyanoborate hydride (500 mg) is added, followed by overnight stirring. The target substance (0.98 g) is obtained after purification by means of dialyzation and lyophilization.

Figure 23:
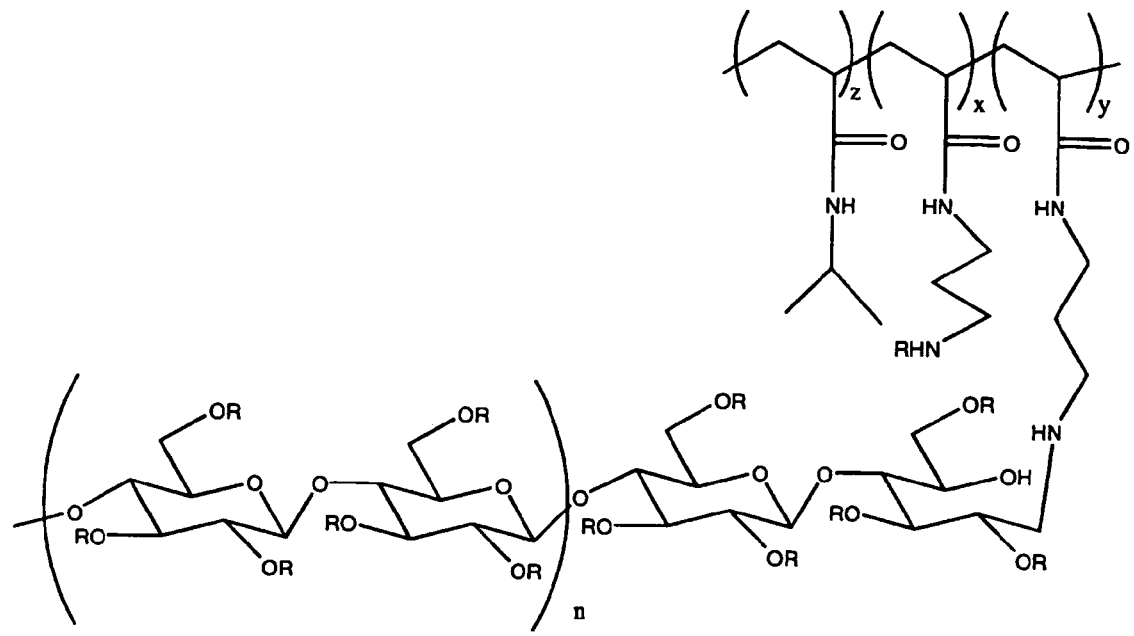
FIG. 23 is a structural formula of synthesis example 21.
Figure 23:
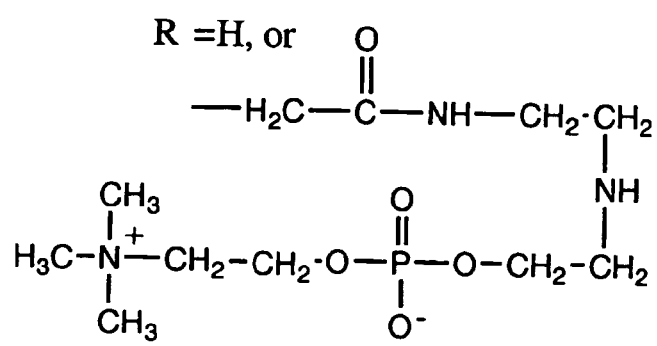

The structural formula is shown in FIG. 23.

The polysaccharides of the present invention (Synthesis examples 8-15) synthesized as described above were used for human blood hemolysis tests conducted with the following procedure.

"Hemolysis Test"

Human blood is added to a K3 solution containing EDTA (5.5 mg), followed by centrifugation at 200 G for five minutes at 4° C. The obtained blood cells are rinsed three times with phosphate buffer (PBS), and mixed with a PBS solution of the polymer. After a 20-minute incubation at 37° C., centrifugation at 5,300 G for five minutes at 4° C. was conducted. The degree of hemolysis (%) was evaluated from UV absorption (541 nm) of the supernatant.

The degree of hemolysis (%) is determined by the following equation.

Degree of hemolysis (%)={($UV$ absorption of the supernatant of the blood to which the polymer is added)−($UV$ absorption of the supernatant of the blood without the added polymer)}/{($UV$ absorption of the supernatant of the completely hemolyzed blood)−($UV$ absorption of the supernatant of the blood without the added polymer)}×100

Figure 24:
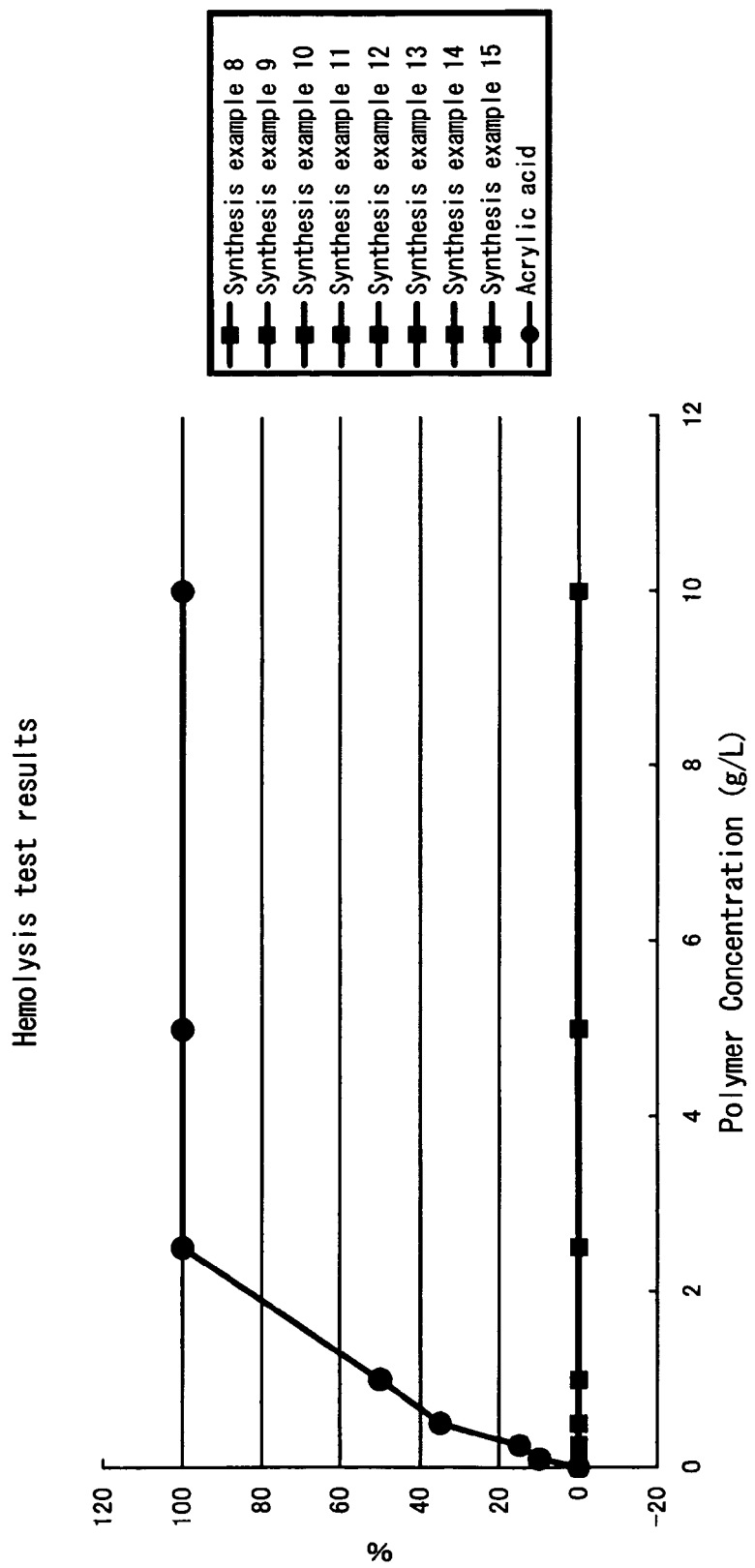
FIG. 24 is a graph showing the hemolysis test results.

The results of the hemolysis test and the degree of hemolysis (%), are shown in Table 1 and FIG. 24. In the graph in FIG. 24, the degree of hemolysis (%) for the polymers to which the phosphorylcholine groups prepared in Synthesis examples 8-15 are introduced is in every case approximately 0%, overlapping with the horizontal axis, and no hemolysis reaction is indicated. This indicates that all of the polysaccharides (polymers) to which phosphorylcholine groups are introduced according to the present invention have a very high blood compatibility.

TABLE 1

"Hemolysis test results"

| Polymer Concentration (g/L) | Synthesis example 8 | Synthesis example 9 | Synthesis example 10 | Synthesis example 11 | Synthesis example 12 | Synthesis example 13 | Synthesis example 14 | Synthesis example 15 | Acrylic acid |
|---|---|---|---|---|---|---|---|---|---|
| 0    | 0     | 0    | 0    | 0    | 0    | 0    | 0     | 0    | 0   |
| 0.1  | 0.01  | 0    | 0.01 | 0.01 | 0    | 0    | 0.02  | 0    | 10  |
| 0.25 | 0.02  | 0    | 0.01 | 0.01 | 0    | 0    | 0.03  | 0    | 15  |
| 0.5  | 0.03  | 0    | 0.05 | 0.01 | 0    | 0    | 0.035 | 0    | 35  |
| 1    | 0.02  | 0    | 0.1  | 0.03 | 0    | 0    | 0.04  | 0.1  | 50  |
| 2.5  | 0.02  | 0.05 | 0.1  | 0.03 | 0    | 0    | 0.04  | 0.1  | 100 |
| 5    | 0.025 | 0.1  | 0.1  | 0.04 | 0.11 | 0.16 | 0.05  | 0.15 | 100 |
| 10   | 0.05  | 0.1  | 0.1  | 0.05 | 0.4  | 0.11 | 0.07  | 0.2  | 100 |

INDUSTRIAL APPLICABILITY

The phosphorylcholine group-containing polysaccharide of the present invention has high biocompatibility and moisture retention and is a useful polymer material; it has a variety of applications such as artificial organs, biomembranes, coating agents for medical tools, drug delivery, and as cosmetic ingredients.

The manufacturing method of the present invention has a great advantage in that it allows flexible designing of phosphorylcholine group-containing polymers ideal for biocompatible polymer materials.

For example, initially the most preferable material for the application can be obtained through a designing process unrestricted by the presence of phosphorylcholine groups by introducing hydrophobic groups into the polysaccharide, for example. Subsequently, a desired quantity of phosphorylcholine groups can be easily added to obtain the target functional polymer material.

The invention claimed is:

1. A polysaccharide having a phosphorylcholine group represented by one of the following general formulas (2)-(10):

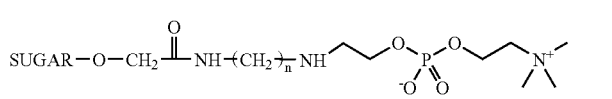
(2)

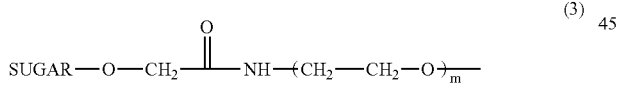
(3)

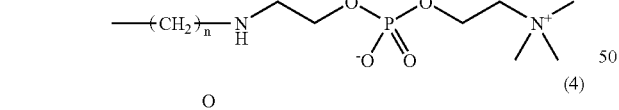
(4)

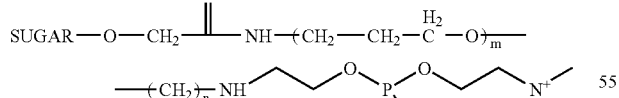
(5)

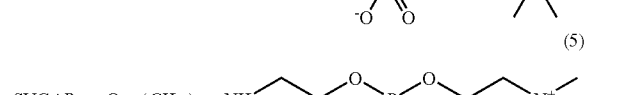
(6)

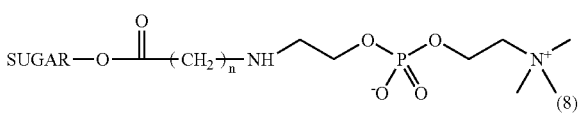
(7)

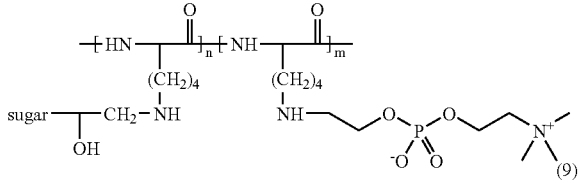
(8)

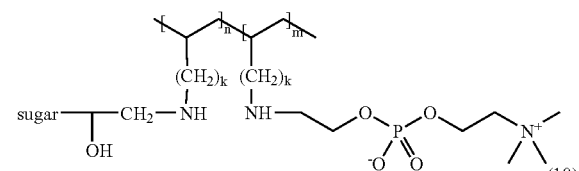
(9)

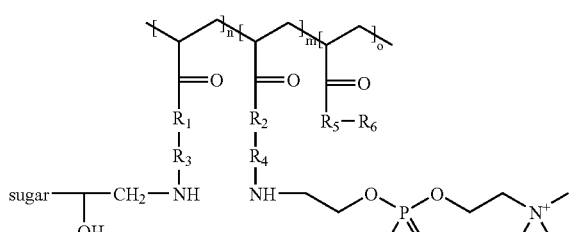
(10)

wherein, in general formulas (2)-(7), n denotes an integer 1-22; in general formulas 3 and 4 m denotes an integer 1-22;

in general formulas (2)-(7), SUGAR denotes a polysaccharide;

in general (10), R1, R2, and R5 denote O, NH, or a tertiary amine;

R3 and R4 are straight chain or branched alkylenes having 1-22 carbon atoms, or ethylene oxide having 1-20 repeat units;

R6 denotes a hydrocarbon including aromatic hydrocarbons or a perfluoroalkylene group having 1-22 carbon atoms;

K denotes an integer 0-6;

in formulas (8),(9) and (10), n, m and q denote positive integers, and

"sugar" denotes a polysachharide.

* * * * *